US008927776B2

(12) United States Patent
Franke et al.

(10) Patent No.: US 8,927,776 B2
(45) Date of Patent: Jan. 6, 2015

(54) METHOD FOR HYDROFORMYLATION OF UNSATURATED COMPOUNDS

(75) Inventors: Robert Franke, Marl (DE); Matthias Beller, Nienhagen (DE); Ralf Jackstell, Cuxhaven Altenwalde (DE); Reiko Jennerjahn, Sanitz (DE); Irene Piras, Alghero (IT)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/883,808

(22) PCT Filed: Oct. 24, 2011

(86) PCT No.: PCT/EP2011/068522
§ 371 (c)(1),
(2), (4) Date: Oct. 2, 2013

(87) PCT Pub. No.: WO2012/062558
PCT Pub. Date: May 18, 2012

(65) Prior Publication Data
US 2014/0024860 A1      Jan. 23, 2014

(30) Foreign Application Priority Data
Nov. 8, 2010  (DE) .................. 10 2010 043 558

(51) Int. Cl.
| C07C 45/50 | (2006.01) |
| C07C 45/27 | (2006.01) |
| C07F 9/145 | (2006.01) |
| C07F 9/50 | (2006.01) |
| C07F 9/572 | (2006.01) |
| C07F 9/6568 | (2006.01) |

(52) U.S. Cl.
CPC ............... C07C 45/27 (2013.01); C07C 45/50 (2013.01); C07F 9/145 (2013.01); C07F 9/5022 (2013.01); C07F 9/5726 (2013.01); C07F 9/65683 (2013.01); C07C 2101/14 (2013.01); C07C 2101/16 (2013.01); C07C 2101/18 (2013.01)
USPC .......................................... 568/444; 568/454

(58) Field of Classification Search
USPC ................................. 568/444, 454
See application file for complete search history.

(56) References Cited

U.S. PATENT DOCUMENTS

| 7,193,116 B2 | 3/2007 | Moeller et al. |
| 7,317,130 B2 | 1/2008 | Möller et al. |
| 7,495,134 B2 | 2/2009 | Hess et al. |
| 7,589,081 B2 | 9/2009 | Zapf et al. |
| 2011/0130595 A1 | 6/2011 | Lueken et al. |
| 2012/0123169 A1 | 5/2012 | Kaizik et al. |
| 2012/0190895 A1 | 7/2012 | Kaizik et al. |
| 2012/0197025 A1 | 8/2012 | Christiansen et al. |
| 2013/0030233 A1 | 1/2013 | Boeing et al. |

FOREIGN PATENT DOCUMENTS

| WO | WO 2011/107441 A1 | 9/2011 |
| WO | WO 2012/041846 A1 | 4/2012 |

OTHER PUBLICATIONS

Rosales et al. Kinetics and mechanisms of homogeneous catalytic reactions Part 7. Hydroformylation of 1-hexene catalyzed by cationic complexes of rhodium and iridium containing PPh3. Journal of Molecular Catalysis A: Chemical, vol. 270 (2007), pp. 250-256.*
Dubs et al. Synthesis of a Library of Iridium-Containing Dinuclear Complexes with Bridging PNNN and PNNP Ligands (BL), [LM (u-BL) M'L']BF4. 2. Preparation, Basic Coordination Properties, and Reactivity of the Carbonyl Complexes. Organometallics, vol. 25, 2006, pp. 1359-1367.*
U.S. Appl. No. 13/822,650, filed Mar. 13, 2013, Franke, et al.
U.S. Appl. No. 13/582,265, filed Mar. 11, 2013, Christiansen, et al.
U.S. Appl. No. 13/703,925, filed Feb. 27, 2013, Franke, et al.
U.S. Appl. No. 13/988,431, filed May 20, 2013, Nordhoff, et al.

* cited by examiner

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to a method for hydroformylation of unsaturated compounds such as olefins and alkynes using mixtures of synthesis gas ($CO/H_2$), in which either the unsaturated compounds and a catalyst are heated to a reaction temperature of 60 to 200° C. and the synthesis gas is then added, or the unsaturated compounds and the catalyst are brought into contact with pure CO at normal temperature in a preformation step, then are heated to reaction temperature and on reaching the reaction temperature the CO is replaced by the synthesis gas. The pressure is 1 to 200 bar and the $CO:H_2$ ratio in the synthesis gas is in the range from 1:1 to 50:1. The iridium catalyst used comprises a phosphorus-containing ligand in the iridium:ligand ratio in the range from 1:1 to 1:100. With high catalyst activities and low catalyst use, very high turnover frequencies are achieved.

20 Claims, No Drawings

METHOD FOR HYDROFORMYLATION OF UNSATURATED COMPOUNDS

CROSS REFERENCE TO RELATED APPLICATIONS

The present application is a 35 U.S.C. §371 national stage patent application of International patent application PCT/EP2011/068522, filed on Oct. 24, 2011, published as WO/2012/062558 on May 18, 2012, the text of which is incorporated by reference, and claims the benefit of the filing date of German application no. 10 2010 043 558.9, filed on Nov. 8, 2010, the text of which is also incorporated by reference.

The present invention relates to a method for hydroformylation of unsaturated compounds for the preparation of aldehydes using catalysts based on iridium complexes.

PRIOR ART

Aldehydes, in particular linear aldehydes such as butyraldehyde, valeraldehyde, hexanal and octanal, are of technical importance as starting products for plasticizer alcohols and surfactants. In addition, linear and branched aldehydes are prepared for a multiplicity of applications as special chemicals and fine chemicals. The most important method used in industry for the preparation of linear aldehydes is hydroformylation or the oxo reaction, in which olefins are reacted with synthesis gas in the presence of rhodium or cobalt catalysts (Scheme 1).

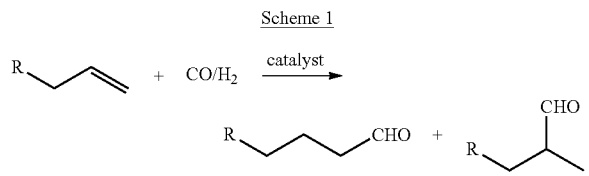

Scheme 1

Review articles that describe this methodology are found, for example, in B. Cornils, W. A. Herrmann, Applied homogeneous catalysis with organometallic compounds, Vol. 1, VCH, Weinheim 2002. In total, in the year 2008 more than 8 million tonnes of oxo products were produced by means of hydroformylation.

Catalysts that are generally used in the course of the hydroformylation reaction are rhodium and cobalt compounds in the presence of ligands. Although both rhodium and cobalt complexes are employed in oxo reactions, it is generally accepted that rhodium(I) compounds form the most active catalysts for this reaction. Unfortunately, rhodium compounds especially are comparatively expensive noble metal complexes. Thus rhodium counts among the most expensive metals in general.

Particularly active rhodium catalysts are formed with phosphite ligands. These ligands have the problem that they are sensitive to hydrolysis of the P—O bond and that they are prone to decomposition during temperature-intensive workup (e.g. distillation). More stable ligands are phosphanes, which, however, only form hydroformylation catalysts that are not very active, for example, for hydroformylating internal olefins sufficiently quickly. A general problem in the development of novel catalyst systems for hydroformylation reactions is the fact that no methods exist for rationally predicting the activity and selectivity of novel catalysts.

Novel hydroformylation catalysts are of interest for the hydroformylation both of terminal as well as internal olefins or olefin mixtures. For fine chemical applications, the tolerance to functional groups is an important criterion. In addition, it is desirable to develop active hydroformylation catalysts based on more cost-effective metals.

In this connection, iridium complexes have hitherto also been described sporadically in the literature. Iridium salts were in past years on average more cost-effective by the factor 5-10 in comparison to the corresponding rhodium compounds. On account of the high hydrogenating activity of the iridium complexes, however, to date no highly selective hydroformylations are known, as relatively large amounts of olefin are hydrogenated to give undesired alkane by-products. Examples of reactions of this type were described by E. Mieczynska et al. (*J. Mol. Catal.* 2005, 237, 246-253), C. M. Crudden and H. Alper (*J. Org. Chem.* 11994, 59, 3091-3097) as well as M. A. Moreno et al. (*J. Catal.* 2003, 215, 326-331) and M. Rosales et al. (*J. Mol. Catal.* 2007, 270, 250-256).

In U.S. Pat. No. 3,239,571, although iridium-based hydroformylations are described, on account of the high hydrogenating activity the aldehydes formed in situ are directly reacted further to give the corresponding alcohols.

In addition, the low activity of the iridium catalysts is a great problem for technical applications, as GB 1 367 623 discloses in 2 examples in hydroformylation under extreme, technically and economically impractical conditions. Thus Protzmann and Wiese (*Erdöl Erdgas kohle* 2001, 117, 235-240) describe that rhodium carbonyl complexes are more active by the factor 10000 than corresponding iridium carbonyl complexes. In accord with this finding, iridium complexes were employed for mechanistic studies on account of their lower activity in order to study and to isolate catalysis intermediates.

In summary, it can be stated that no method for hydroformylation using iridium-containing catalysts is known that has both high catalyst activities with TOF>100 h$^{-1}$, and at the same time achieves high chemoselectivities for the aldehyde (>90%) and a predominant regioselectivity for unbranched n-isomer. These target figures are essential to achieve industrial conversions.

OBJECT

For the abovementioned reasons, there is a great need for novel improved methods using iridium-containing catalyst systems that have high activity and that do not exhibit the disadvantages of the known iridium-containing catalysts. The invention is based on the object of making available methods for hydroformylation of terminal and internal olefins and olefin mixtures in high yield as well as high catalyst productivity and chemoselectivity for aldehydes, where a predominant regioselectivity for the un-branched n-isomer is achieved and iridium is used instead of rhodium.

SUMMARY OF THE INVENTION

This object is achieved by hydroformylation of unsaturated compounds using mixtures of synthesis gas (CO/H$_2$), an excess of carbon monoxide being used and the synthesis gas only being added on reaching the reaction temperature, or a preformation step with addition of pure carbon monoxide being inserted upstream to suppress undesired hydrogenation as a side reaction, in the presence of iridium salts and/or iridium complexes with phosphorus-containing ligands.

DETAILED DESCRIPTION OF THE INVENTION

The invention relates to a method for hydroformylation of unsaturated compounds using mixtures of carbon monoxide and hydrogen as synthesis gas and is characterized in that
(a1) the unsaturated compounds and a catalyst are heated to a reaction temperature of 60 to 200° C. and
(a2) the synthesis gas is then added
or
(b1) the unsaturated compounds and the catalyst are brought into contact with pure CO at normal temperature in a preformation step,
(b2) the mixture is heated to the reaction temperature of 60 to 200° C. and
(b3) on reaching the reaction temperature the CO is replaced by the synthesis gas,
where the reaction pressure is in the range from 0.1 to 20.0 MPa, the $CO:H_2$ ratio in the synthesis gas is in the range from 1:1 to 50:1 and the unsaturated compound is reacted in the presence of a polar solvent and of an iridium catalyst, the iridium-containing catalyst comprising a phosphorus-containing ligand in the iridium:ligand ratio in the range from 1:1 to 1:100 and all ratios being molar ratios.

A mixture of carbon monoxide and hydrogen is used as synthesis gas, an excess of carbon monoxide being employed. This prevents undesired hydrogenating side reactions. The excess $CO:H_2$ is particularly preferably 1:1 to 10:1.

The synthesis gas overall pressure is preferably 0.1 to 10.0 MPa, in particular 0.5 to 10.0 MPa and particularly preferably 1.0 to 5.0 MPa.

To suppress undesired hydrogenating side reactions, it is particularly advantageous to carry out the method such that a CO excess is contained in the reaction mixture even at normal temperature.

Normal temperature is understood as meaning the range 15-25° C.

The target reaction preferably proceeds at temperatures from 80 to 180° C.; particularly preferably at 100 to 160° C.

For the method according to the invention, solvents are employed for the catalyst. Solvents used are in general polar inert organic solvents or/and water. Mentioned by way of example are dipolar aprotic solvents, aliphatic ethers, amides, aromatic compounds, alcohols and esters as well as mixtures thereof. Dipolar solvents or ethers such as, for example, tetrahydrofuran are particularly preferred.

As iridium source, as a precursor all iridium-containing salts and complexes can be used that form iridium carbonyl complexes under the reaction conditions. Mentioned by way of example are Ir(I) and Ir(III) halides (e.g. chloro-1,5-cyclooctadieneiridium(I) dimer, iridium(III) chloride), Ir(I) and Ir(III) carboxylates, Ir(III) and Ir(IV) iridates (e.g. potassium hexachloroiridate(IV)), Ir-carbonyl complexes (e.g. iridium carbonyl), Ir-olefin, Ir-hydrido, iridium-arene and iridium-allyl complexes (e.g. hydridocarbonyltris(triphenylphosphine)iridium(I), 1,5-cylooctadiene($n^6$-indenyl)iridium(I)). The iridium compounds can be present in different oxidation stages (−1 to +V), which react with synthesis gas and P-containing ligands to give the corresponding active iridium(hydrido)(carbonyl) complexes.

A particularly preferred precursor is iridium cyclooctadiene acetylacetonate.

To achieve the desired catalyst selectivities and catalyst activities, it is necessary to add a phosphorus-containing ligand. In the present method, this ligand is added to iridium in an excess. The iridium to ligand ratio is preferably 1:1 to 1:50, in particularly preferred embodiments 1:1 to 1:8.

As ligands, any desired phosphorus-containing ligands can be employed that can form a coordinative bond to the iridium centre. By way of example, phosphines (e.g. triarylphosphines such as triphenylphosphine, tri-o-tolylphosphine, Xanthphos (9,9-dimethyl-9H-xanthen-4,5-diyl)bis(diphenylphosphine), BINAP (2,2'-bis-(diphenylphosphino)-1,1'-binaphthyl), NaPhos (2,2'-bis((diphenylphosphino)methyl)-1,1'-binaphthyl), Dppf (1,1'-bis(diphenylphosphino)ferrocene), as well as trialkylphosphines such as tricyclohexylphosphine), phosphites (e.g. tris(2-di-t-butyl)phosphite, 6,6'-[(3,3'-di-t-butyl-5,5'-dimethoxy-1,1'-biphenyl-2,2'-diyl)bis(oxy)]bis(dibenzo[d,f][1,3,2]dioxaphosphepine)), phosphoramidites (e.g. MonoPhos (N,N-dimethyldinaphtho[2,1-d:1',2'-f][1,3,2]dioxaphosphepine-4-amine), MorfPhos (4-(dinaphtho[2,1-d:1',2'-f][1,3,2]dioxaphosphepin-4-yl)morpholine), PipPhos (1-(dinaphtho[2,1-d:1',2'-f][1,3,2]dioxaphosphepin-4-yl)piperidine)), phosphonites and phosphinites (e.g. CARBOPHOS (methyl α-D-glucopyranoside-2,6-dibenzoate-3,4-di(bis(3,5-dimethylphenyl)phosphinite))) may be mentioned by way of example. The ligands here can bind both in monodentate and multidentate form. Monodentate and bidentate ligands are preferred.

Particularly preferred ligands are selected from the group containing triphenylphosphine, 2-(diphenylphosphino)-1-phenyl-1H-pyrrole, tricyclohexylphosphine and (11bS)-4-tert-butyl-4,5-dihydro-3H-dinaphtho[2,1-c:1',2'-e]phosphepine.

Unsaturated compounds that can be reacted selectively with the catalyst systems mentioned are alkynes and olefins, olefins being preferred. Terminal alkenes, cycloalkenes and aromatic olefins having a carbon number between 2 and 20 and their mixtures are particularly preferred. Olefins having 4 to 12 carbon atoms and their mixtures are very particularly preferred.

The method according to the invention has particularly proved to be of value for the production of aldehydes having 3 to 21 carbon atoms. In particular, the production of aldehydes having 5-13 carbon atoms is preferred.

The olefins and alkynes can be functionalized. Without claiming to be complete, mention may be made here of unsaturated alcohols, ethers, amines, esters, carboxylic acids, amides, urethanes, halides, aldehydes, ketones and epoxides as substrates.

With the method according to the invention, turnover numbers [(TON)=(turnover frequency (TOF)×hours reaction time)] of the catalysts of the order of magnitude of 10,000 and more can be realized. Therefore between 0.001 and 0.4 mol % of iridium—based on the olefin substrate—is typically employed. Preferably, between 0.002 and 0.08, particularly preferably between 0.003 and 0.05, mol % and especially preferably between 0.02 and 0.4 mol % of iridium—based on the olefin substrate—is employed.

On account of the significantly improved catalyst activities, it is possible in the method according to the invention to use small amounts of catalyst.

The method according to the invention is particularly surprising and novel in as much as in the past no highly selective hydroformylations of olefins using iridium complexes with adequate activity have been described. The method described here shows for the first time that good yields and selectivities of aldehydes are possible under the conditions according to the invention. The particular advantages of the novel method consist in the fact that iridium as a catalyst metal is markedly more cost-effective in comparison to rhodium. To realize this advantage, it is necessary that high catalyst activities are achieved using iridium complexes. This is possible by means of the method according to the invention. Thus 1-octene, for example, is reacted with a turnover frequency of nearly 200 $h^{-1}$.

The aldehydes produced according to the invention can be employed, inter alia, as intermediates for plasticizer alcohols, as surfactants and as precursors for pharmaceuticals and agrochemicals as well as components for polymers.

EXAMPLES

The examples below serve to illustrate the method according to the invention without restricting it thereto.

General working procedure for the hydroformylation reaction of olefins by means of an iridium/phosphine catalyst:

A mixture of 10.2 mmol of alkene, the corresponding amount of Ir(cod)acac as a catalyst precursor (with 0.2 mol % of catalyst:0.02 mmol=8.15 mg), the corresponding amount of ligand and 6 ml of absolute THF as a solvent is brought to reaction in a 25 ml autoclave from Parr. For this, different variants of reaction control are possible (see Examples 1-11). The mixture is stirred for 16 h. After the specified reaction time and cooling and depressurization of the autoclave, 1 ml of isooctane is added as an internal standard and the reaction mixture is analysed by gas chromatography. For general details see footnote [a] below Table 1.

The influence of pressure in the hydroformylation of 1-octene as a substrate (Examples 1-10) without use of the preformation step is shown in Table 1. The entry 1 in Table 1, which documents the prior art as a comparison example, is noteworthy in this connection. The reaction conditions used there and the reaction control applied largely correspond to the teaching described in GB 1 367 623. This leads to a low yield of only 35 mass % of aldehydes with simultaneous formation of 62 mass % of octane as an undesired by-product. Further, an n:iso ratio of 58/42 of the aldehydes formed is achieved by the nearly non-existent regioselectivity.

TABLE 1

Ir-catalysed hydroformylation of 1-octene without a preformation step:

| No. [a] | Pressure [MPa] | T [° C.] | Yield[g] [mass %] | n/iso | H[h] [mass %] | TOF[i] [$h^{-1}$] |
|---|---|---|---|---|---|---|
| 1[b] | 4.6 (1 CO/1 $H_2$) | 120 | 35 | 58/42 | 62 | 11 |
| 2[c] | 4.0 (1 CO/1 $H_2$) | 100 | 69 | 74/26 | 20 | 22 |
| 3[c] | 4.0 (1 CO/1 $H_2$) | 80 | 13 | 75/25 | 3 | 4 |
| 4[c] | 4.0 (1 CO/1 $H_2$) | 120 | 70 | 71/29 | 29 | 22 |
| 5[c] | 5.0 (1 CO/1 $H_2$) | 100 | 62 | 74/26 | 17 | 19 |
| 6[c] | 2.0 (1 CO/1 $H_2$) | 100 | 74 | 75/25 | 20 | 23 |
| 7[c] | 1.0 (1 CO/1 $H_2$) | 100 | 72 | 75/25 | 23 | 22 |
| 8[d] | 2.3 (2 CO/1 $H_2$) | 100 | 73 | 75/25 | 14 | 23 |
| 9[e] | 2.3 (2 CO/1 $H_2$) | 100 | 77 | 76/24 | 12 | 24 |
| 10[f] | 2.3 (3 CO/1 $H_2$) | 100 | 71 | 76/24 | 8 | 22 |

[a] 10.2 mmol of 1-octene, Ir(cod)acac 0.2 mol % (8.1 mg), 0.44 mol % of $PPh_3$, 6 ml of THF, 16 h.
[b] Synthesis gas (CO/$H_2$ = 1:1) added at 20° C.
[c] Synthesis gas (CO/$H_2$ = 1:1) added if reaction temperature reached.
[d] 0.7 MPa CO and 13 bar synthesis gas (CO/$H_2$ = 1:1) added at 100° C.
[e] 0.7 MPa CO added at 20° C. and 1.3 MPa synthesis gas (CO/$H_2$ = 1:1) added at 100° C.
[f] 1.0 MPa CO added at 20° C. and 1.0 MPa synthesis gas (CO/$H_2$ = 1:1) added at 100° C.
[g] GC yields.
[h] Octane;
[i] calculated on the aldehyde yield

Example 1, Comparison Example

Table 1, Entry 1

10.2 mmol of 1-octene, Ir(cod)acac 0.2 mol % (8.1 mg), 0.44 mol % $PPh_3$ (11.8 mg) and 6 ml of THF under protective gas (e.g. argon or nitrogen) are transferred to a 25 ml stainless steel autoclave. 4.0 MPa of synthesis gas (CO/$H_2$=1:1) are added at 20° C. The autoclave is heated to 120° C. and a final pressure of the reaction of 4.6 MPa is achieved. The mixture is stirred at this temperature for 16 h. Subsequently, the autoclave is cooled to room temperature and the residual pressure is released. 1 ml of isooctane is added to the reaction solution as an internal standard and the mixture is investigated by gas chromatography. The yield of nonanal is 35% with an n:iso ratio of 58:42. Moreover, 62% of octane is found as hydrogenated starting substance.

Example 2

Table 1, Entry 2

10.2 mmol of 1-octene, Ir(cod)acac 0.2 mol % (8.1 mg), 0.44 mol % of $PPh_3$ (11.8 mg) and 6 ml of THF under protective gas (e.g. argon or nitrogen) are transferred to a 25 ml stainless steel autoclave. The autoclave is heated to 100° C. and 4.0 MPa of synthesis gas (CO:$H_2$=1:1) are injected at this temperature. The mixture is stirred for 16 h at this reaction pressure of 4.0 MPa.

Subsequently, the autoclave is cooled to room temperature and the residual pressure is released. 1 ml of isooctane is added to the reaction solution as an internal standard and the mixture is investigated by gas chromatography. The yield of nonanal is 69% with an n:iso ratio of 74:26. Moreover, 20% of octane is found as a hydrogenated starting substance.

Example 3

Table 1, Entry 3

10.2 mmol of 1-octene, Ir(cod)acac 0.2 mol % (8.1 mg), 0.44 mol % of $PPh_3$ (11.8 mg) and 6 ml of THF are transferred under protective gas (e.g. argon or nitrogen) to a 25 ml stainless steel autoclave. The autoclave is heated to 80° C. and 4.0 MPa of synthesis gas (CO:$H_2$=1:1) are injected at this temperature. The mixture is stirred for 16 h at this reaction pressure of 4.0 MPa.

Subsequently, the autoclave is cooled to room temperature and the residual pressure is released. 1 ml of isooctane is added to the reaction solution as an internal standard and the mixture is investigated by gas chromatography. The yield of nonanal is 13% with an n:iso ratio of 75:25. Moreover, 3% of octane is found as hydrogenated starting substance.

Example 4

Table 1, Entry 4

10.2 mmol of 1-octene, Ir(cod)acac 0.2 mol % (8.1 mg), 0.44 mol % of $PPh_3$ (11.8 mg) and 6 ml of THF under protective gas (e.g. argon or nitrogen) are transferred to a 25 ml stainless steel autoclave. The autoclave is heated to 120° C. and 4.0 MPa of synthesis gas (CO:$H_2$=1:1) are injected at this temperature. The mixture is stirred for 16 h at this reaction pressure of 4.0 MPa.

Subsequently, the autoclave is cooled to room temperature and the residual pressure is released. 1 ml of isooctane is added to the reaction solution as an internal standard and the mixture is investigated by gas chromatography. The yield of nonanal is 70% with an n:iso ratio of 71:29. Moreover, 29% of octane is found as hydrogenated starting substance.

Example 5

Table 1, Entry 5

10.2 mmol of 1-octene, Ir(cod)acac 0.2 mol % (8.1 mg) 0.44 mol % of $PPh_3$ (11.8 mg) and 6 ml of THF under protective gas (e.g. argon or nitrogen) are transferred to a 25 ml stainless steel autoclave. The autoclave is heated to 100° C. and 5.0 MPa of synthesis gas ($CO:H_2=1:1$) are injected at this temperature. The mixture is stirred for 16 h at this reaction pressure of 5.0 MPa.

Subsequently, the autoclave is cooled to room temperature and the residual pressure is released. 1 ml of isooctane is added to the reaction solution as internal standard and the mixture is investigated by gas chromatography. The yield of nonanal is 62% with an n:iso ratio of 74:26. Moreover, 17% of octane is found as hydrogenated starting substance.

Example 6

Table 1, Entry 6

10.2 mmol of 1-octene, Ir(cod)acac 0.2 mol % (8.1 mg), 0.44 mol % of $PPh_3$ (11.8 mg) and 6 ml of THF under protective gas (e.g. argon or nitrogen) are transferred to a 25 ml stainless steel autoclave. The autoclave is heated to 100° C. and 2.0 MPa of synthesis gas ($CO:H_2=1:1$) are injected at this temperature. The mixture is stirred for 16 h at this reaction pressure of 2.0 MPa.

Subsequently, the autoclave is cooled to room temperature and the residual pressure is released. 1 ml of isooctane is added to the reaction solution as internal standard and the mixture is investigated by gas chromatography. The yield of nonanal is 74% with an n:iso ratio of 75:25. Moreover, 20% of octane is found as hydrogenated starting substance.

Example 7

Table 1, Entry 7

10.2 mmol of 1-octene, Ir(cod)acac 0.2 mol % (8.1 mg), 0.44 mol % of $PPh_3$ (11.8 mg) and 6 ml of THF are transferred under protective gas (e.g. argon or nitrogen) to a 25 ml stainless steel autoclave. The autoclave is heated to 100° C. and 1.0 MPa of synthesis gas ($CO:H_2=1:1$) is injected at this temperature. The mixture is stirred for 16 h at this reaction pressure of 1.0 MPa.

Subsequently, the autoclave is cooled to room temperature and the residual pressure is released. 1 ml of isooctane is added to the reaction solution as internal standard and the mixture is investigated by gas chromatography. The yield of nonanal is 72% with an n:iso ratio of 75:25. Moreover, 23% of octane is found as hydrogenated starting substance.

Example 8

Table 1, Entry 8

10.2 mmol of 1-octene, Ir(cod)acac 0.2 mol % (8.1 mg), 0.44 mol % of $PPh_3$ (11.8 mg) and 6 ml of THF are transferred under protective gas (e.g. argon or nitrogen) to a 25 ml stainless steel autoclave. The autoclave is heated to 100° C. and 0.7 MPa of carbon monoxide (CO) and subsequently 1.3 MPa of synthesis gas ($CO:H_2=1:1$) are injected at this temperature in a temporally direct sequence. A final pressure of the reaction of 2.3 MPa is achieved and the mixture is stirred for 16 h at a $CO:H_2$ ratio of 2.08:1. Subsequently, the autoclave is cooled to room temperature and the residual pressure is released. 1 ml of isooctane is added to the reaction solution as internal standard and the mixture is investigated by gas chromatography. The yield of nonanal is 73% with an n:iso ratio of 75:25. Moreover, 14% of octane is found as hydrogenated starting substance.

Example 9

Table 1, Entry 9

10.2 mmol of 1-octene, Ir(cod)acac 0.2 mol % (8.1 mg), 0.44 mmol % of $PPh_3$ (11.8 mg) and 6 ml of THF under protective gas (e.g. argon or nitrogen) are transferred to a 25 ml stainless steel autoclave. 0.7 MPa of carbon monoxide is injected at 20° C. The autoclave is heated to 100° C. and 1.3 MPa of synthesis gas ($CO:H_2=1:1$) are injected at this temperature. A final pressure of the reaction of 2.3 MPa is achieved and the mixture is stirred for 16 h at a $CO:H_2$ ratio of 2.08:1. Subsequently, the autoclave is cooled to room temperature and the residual pressure is released. 1 ml of isooctane is added to the reaction solution as internal standard and the mixture is investigated by gas chromatography. The yield of nonanal is 77% with an n:iso ratio of 76:24. Moreover, 12% of octane is found as hydrogenated starting substance.

Example 10

Table 1, Entry 10

10.2 mmol 1-octene, Ir(cod)acac 0.2 mol % (8.1 mg), 0.44 mol % of $PPh_3$ (11.8 mg) and 6 ml of THF are transferred under protective gas (e.g. argon or nitrogen) to a 25 ml stainless steel autoclave. 1.0 MPa of carbon monoxide is injected at 20° C. The autoclave is heated to 100° C. and 1.0 MPa of synthesis gas ($CO:H_2=1:1$) is injected at this temperature. A final pressure of the reaction of 2.3 MPa is achieved and the mixture is stirred for 16 h at a $CO:H_2$ ratio of 3:1. Subsequently, the autoclave is cooled to room temperature and the residual pressure is released. 1 ml of isooctane is added to the reaction solution as internal standard and the mixture is investigated by gas chromatography. The yield of nonanal is 71% with an n:iso ratio of 76:24. Moreover, 8% of octane is found as hydrogenated starting substance.

In Table 2 below (Examples 11-26), ligand effects in the hydroformylation of 1-octene as a substrate are shown with use of the preformation step (1).

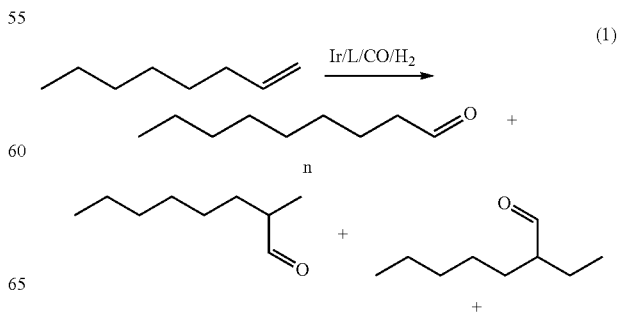

(1)

-continued

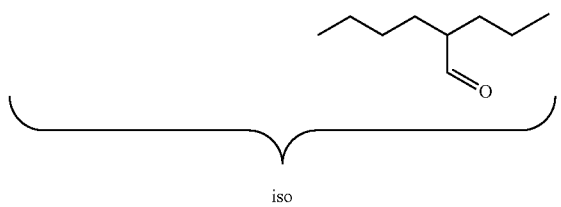

iso

Again, entry 1 of Table 2 serves as a comparison example for the documentation of the prior art. Without use of a ligand, despite a preformation step the yield of aldehydes falls to 30 mass % with extensive loss of the regioselectivity with an n:iso ratio of only 52/48 of the aldehydes formed. In addition, the known hydrogenating activity is confirmed by the formation of 65 mass % of octane as an undesired by-product.

As described and claimed beforehand, water with a suitable ligand can also be used as a polar solvent, such as entry 16 of Table 2 shows in Example 26.

TABLE 2

Ir-catalysed hydroformylation of 1-octene with a preformation step: ligand effects

| No.[a] | Ligand(L) | L/Ir | Yield[e] [mass %] | n/iso | H[f] [mass %] | TOF[g] [h$^{-1}$] |
|---|---|---|---|---|---|---|
| 1[b] | — | — | 30 | 52/48 | 65 | 8 |
| 2[b] | PPh$_3$ | 1 | 44 | 72/28 | 43 | 11 |
| 3[b] | PPh$_3$ | 4 | 61 | 76/24 | 13 | 15 |
| 4 | PPh$_3$ | 3 | 81 | 76/24 | 12 | 21 |
| 5 | PPh$_3$ | 2.2 | 83 | 76/24 | 12 | 21 |
| 6[c] | HIrCO(PPh$_3$)$_3$ | 3 | 80 | 76/24 | 13 | 20 |
| 7 | ((MeO)$_3$C$_6$H$_2$)$_3$P | 2.2 | 43 | 86/14 | 37 | 11 |
| 8 | L1 | 2.2 | 38 | 71/29 | 52 | 10 |
| 9 | dppb | 1 | 41 | 74/26 | 9 | 10 |
| 10 | L2 | 2.2 | 85 | 72/28 | 12 | 21 |
| 11 | PCy$_3$ | 2.2 | 26 | 67/33 | 55 | 7 |
| 12 | L3 | 2.2 | 7 | 74/26 | 3 | 2 |
| 13 | L4 | 2.2 | 58 | 77/23 | 16 | 15 |
| 14 | Ir$_2$(CO)$_6$(PPh$_3$)$_2$ | 1 | 46 | 74/26 | 41 | 12 |
| 15[d] | PPh$_3$ | 8 | 65 | 76/24 | 19 | 163 |
| 16 | L5 | 2 | 17 | 73/27 | 40 | 4 |

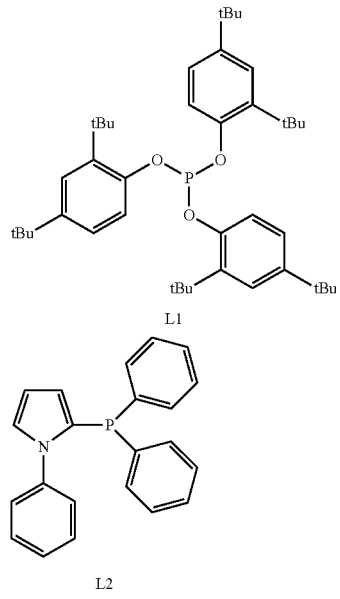

TABLE 2-continued

Ir-catalysed hydroformylation of 1-octene with a preformation step: ligand effects

| No.[a] | Ligand(L) | L/Ir | Yield[e] [mass %] | n/iso | H[f] [mass %] | TOF[g] [h$^{-1}$] |
|---|---|---|---|---|---|---|

[a] 10.2 mmol of 1-octene, Ir(cod)acac 0.2 mol % (8.1 mg), 6 ml of THF, 100° C., 2.0 MPa of CO/H$_2$ (2/1), 0.7 MPa of CO at 15-25° C. and 1.3 MPa of synthesis gas (CO/H$_2$=1:1) at 100° C., 20 h. [b] as [a] but 16 h. [c] 0.2 mol % HIrCO(PPh$_3$)$_3$. [d] as [a] but 0.02 mol % Ir(cod)acac. [e] GC yields. [f] octane; NMP=N-methylpyrrolidone, PCy$_3$=tricyclohexylphosphine, Ir(cod)acac=iridium cyclooctadiene acetylacetonate, dppb=1,4-bis(diphenylphosphino)butane, THF=tetrahydrofuran, H=hydrogenation product. [g] calculated on the aldehyde yield Example 11. Comparison Example Table 2, Entry 1

10.2 mmol of 1-octene (1.1 g), Ir(cod)acac 0.2 mol % (8.1 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:H$_2$=1:1) are additionally injected at this temperature. A final pressure of the reaction of 2.3 MPa is achieved. The autoclave is stirred at this temperature for 16 h at a CO:H$_2$ ratio of 2.0 8:1, subsequently cooled and the residual pressure is released. The reaction mixture is investigated by gas chromatography. 30% of nonanal is determined with an n:iso ratio of 52:48. 65% of octane is detected as hydrogenated starting substance.

Example 12

Table 2, Entry 2

10.2 mmol of 1-octene (1.1 g), Ir(cod)acac 0.2 mol % (8.1 mg), 0.2 mol % of PPh$_3$ (5.3 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:$H_2$=1:1) are additionally injected at this temperature. A final pressure of the reaction of 2.3 MPa at a CO:$H_2$ ratio of 2.08:1 is achieved. The autoclave is stirred at this temperature for 20 h, subsequently cooled and the residual pressure is released. The reaction mixture is investigated by gas chromatography. 44% of nonanal with an n:iso ratio of 72:28 is determined. 43% of octane is detected as hydrogenated starting substance.

Example 13

Table 2, Entry 3

10.2 mmol of 1-octene (1.1 g), Ir(cod)acac 0.2 mol % (8.1 mg), 0.8 mol % of $PPh_3$ (21.2 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:$H_2$=1:1) are additionally injected at this temperature. A final pressure of the reaction of 2.3 MPa at a CO:$H_2$ ratio of 2.08:1 is achieved. The autoclave is stirred at this temperature for 16 h, subsequently cooled and the residual pressure is released. The reaction mixture is investigated by gas chromatography. 61% of nonanal is determined with an n:iso ratio of 76:24. 13% of octane is detected as hydrogenated starting substance.

Example 14

Table 2, Entry 4

10.2 mmol of 1-octene (1.1 g), Ir(cod)acac 0.2 mol % (8.1 mg), 0.6 mol % of $PPh_3$ (15.9 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:$H_2$=1:1) are additionally injected at this temperature. A final pressure of the reaction of 2.3 MPa at a CO:$H_2$ ratio of 2.08:1 is achieved. The autoclave is stirred at this temperature for 20 h, subsequently cooled and the residual pressure is released. The reaction mixture is investigated by gas chromatography. 81% of nonanal is determined with an n:iso ratio of 76:24. 12% of octane as hydrogenated starting substance is detected.

Example 15

Table 2, Entry 5

10.2 mmol of 1-octene (1.1 g), Ir(cod)acac 0.2 mol % (8.1 mg), 0.44 mol % of $PPh_3$ (11.66 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:$H_2$=1:1) are additionally injected at this temperature. A final pressure of the reaction of 2.3 MPa at a CO:$H_2$ ratio of 2.08:1 is achieved. The autoclave is stirred at this temperature for 20 h, subsequently cooled and the residual pressure is released. The reaction mixture is investigated by gas chromatography. 83% of nonanal is determined with an n:iso ratio of 76:24. 12% of octane as hydrogenated starting substance is detected.

Example 16

Table 2, Entry 6

10.2 mmol of 1-octene (1.1 g), HIr($PPh_3$)$_3$CO 0.2 mol % (20.56 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:$H_2$=1:1) are additionally injected at this temperature. A final pressure of 2.3 MPa at a CO:$H_2$ ratio of 2.08:1 is achieved. The autoclave is stirred at this temperature for 20 h, subsequently cooled and the residual pressure is released. The reaction mixture is investigated by gas chromatography. 80% of nonanal is determined with an n:iso ratio of 76:24. 13% of octane is detected as hydrogenated starting substance.

Example 17

Table 2, Entry 7

10.2 mmol of 1-octene (1.1 g), Ir(cod)acac 0.2 mol % (8.1 mg), 0.44 mol % of ((MeO)$_3C_6H_2$)$_3$P (23.9 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:$H_2$=1:1) are additionally injected at this temperature. A final pressure of the reaction of 2.3 MPa at a CO:$H_2$ ratio of 2.08:1 is achieved. The autoclave is stirred at this temperature for 20 h, subsequently cooled and the residual pressure is released. The reaction mixture is investigated by gas chromatography. 43% of nonanal is determined with an n:iso ratio of 86:14. 37% of octane is detected as hydrogenated starting substance.

Example 18

Table 2, Entry 8

10.2 mmol of 1-octene (1.1 g), Ir(cod)acac 0.2 mol % (8.1 mg), 0.44 mol % of tris(2,4-di-t-butylphenyl)phosphite (L1, 29 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:$H_2$=1:1) are additionally injected at this temperature. A final pressure of the reaction of 2.3 MPa at a CO:$H_2$ ratio of 2.08:1 is achieved. The autoclave is stirred at this temperature for 20 h, subsequently cooled and the residual pressure is released. The reaction mixture is investigated by gas chromatography. 38% of nonanal is determined with an n:iso ratio of 71:29. 52% of octane is detected as hydrogenated starting substance.

Example 19

Table 2, Entry 9

10.2 mmol of 1-octene (1.1 g), Ir(cod)acac 0.2 mol % (8.1 mg), 0.2 mol % of 1,4-bis(diphenylphosphino)butane (dppb, 8.7 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas (CO:$H_2$=1:1) are additionally injected at this temperature. A final pressure of the reaction of 2.3 MPa at a CO:$H_2$ ratio of 2.08:1 is achieved. The autoclave is stirred at this temperature for 20 h, subsequently cooled and the residual pressure is released. The reaction mixture is investigated by gas chromatography. 41% of nonanal is determined with an n:iso ratio of 74:26. 9% of octane is detected as hydrogenated starting substance.

Example 20

Table 2, Entry 10

10.2 mmol of 1-octene (1.1 g), Ir(cod)acac 0.2 mol % (8.1 mg), 0.44 mol % of 2-(diphenylphosphino)-1-phenyl-1H-pyrrole (L2, 14.7 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas ($CO:H_2=1:1$) are additionally injected at this temperature. A final pressure of the reaction of 2.3 MPa is achieved at a $CO:H_2$ ratio of 2.08:1. The autoclave is stirred at this temperature for 20 h, subsequently cooled and the residual pressure is released. The reaction mixture is investigated by gas chromatography. 85% of nonanal is determined with an n:iso ratio of 72:28. 12% of octane is detected as hydrogenated starting substance.

Example 21

Table 2, Entry 11

10.2 mmol of 1-octene (1.1 g), Ir(cod)acac 0.2 mol % (8.1 mg), 0.44 mol % of tricyclohexylphosphine (12.6 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas ($CO:H_2=1:1$) are additionally injected at this temperature. A final pressure of the reaction of 2.3 MPa at a $CO:H_2$ ratio of 2.08:1 is achieved. The autoclave is stirred at this temperature for 20 h, subsequently cooled and the residual pressure is released. The reaction mixture is investigated by gas chromatography. 26% of nonanal is determined with an n:iso ratio of 67:33. 55% of octane is detected as hydrogenated starting substance.

Example 22

Table 2, Entry 12

10.2 mmol of 1-octene (1.1 g), Ir(cod)acac 0.2 mol % (8.1 mg), 0.44 mol % of R-S-Josiphos L3 (26.7 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas ($CO:H_2=1:1$) are additionally injected at this temperature. A final pressure of the reaction of 2.3 MPa at a $CO:H_2$ ratio of 2.08:1 is achieved. The autoclave is stirred at this temperature for 20 h, subsequently cooled and the residual pressure is released. The reaction mixture is investigated by gas chromatography. 7% of nonanal is determined with an n:iso ratio of 74:26. 3% of octane is detected as hydrogenated starting substance.

Example 23

Table 2, Entry 13

10.2 mmol of 1-octene (1.1 g), Ir(cod)acac 0.2 mol % (8.1 mg), 0.44 mol % of L4, (11bS)-4-tert-butyl-4,5-dihydro-3H-dinaphtho[2,1-c:1',2'-e]phosphepine (16.5 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas ($CO:H_2=1:1$) are additionally injected at this temperature. A final pressure of the reaction of 2.3 MPa at a $CO:H_2$ ratio of 2.08:1 is achieved. The autoclave is stirred at this temperature for 20 h, subsequently cooled and the residual pressure is released. The reaction mixture is investigated by gas chromatography. 58% of nonanal is determined with an n:iso ratio of 77:23. 16% of octane is detected as hydrogenated starting substance.

Example 24

Table 2, Entry 14

10.2 mmol of 1-octene (1.1 g), 0.1 mol % of $Ir_2(CO)_6(PPh_3)_2$ (11 mg), and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas ($CO:H_2=1:1$) are additionally injected at this temperature. A final pressure of the reaction of 2.3 MPa at a $CO:H_2$ ratio of 2.08:1 is achieved. The autoclave is stirred at this temperature for 20 h, subsequently cooled and the residual pressure is released. The reaction mixture is investigated by gas chromatography. 46% of nonanal is determined with an n:iso ratio of 74:26. 41% of octane is detected as hydrogenated starting substance.

Example 25

Table 2, Entry 15

10.2 mmol of 1-octene (1.1 g), Ir(cod)acac 0.02 mol % (0.81 mg), 0.16 mol % of $PPh_3$ (4.3 mg) and 6 ml of THF are transferred under protective gas (e.g. argon or nitrogen) to a 25 ml autoclave. 0.7 MPa of carbon monoxide is injected at 20° C. The autoclave is heated to 100° C. and 1.3 MPa of synthesis gas ($CO:H_2=1:1$) are additionally injected at this temperature. A final pressure of the reaction of 2.3 MPa is achieved at a $CO:H_2$ ratio of 2.08:1. The autoclave is stirred at this temperature for 20 h, subsequently cooled and the residual pressure is released. The reaction mixture is investigated by gas chromatography. 65% of nonanal is determined with an n:iso ratio of 76:24. 19% of octane is detected as hydrogenated starting substance.

Example 26

Table 2, Entry 16

30.6 mmol of 1-octene (3.3 g), 0.2 mol % (24.3 mg) of Ir(cod)acac, 0.4 mol % (69.5 mg) of sodium 3,3',3''-phosphinetriyltribenzensulphonate, (TPPTS=L 5), and 18 ml of degassed water are transferred under argon to a 100 ml autoclave. 0.7 MPa of carbon monoxide is injected at 20° C. The autoclave is heated to 100° C. and 1.3 MPa of synthesis gas (CO:H$_2$=1:1) are additionally injected at this temperature. A final pressure of the reaction of 2.3 MPa at a CO:H$_2$ ratio of 2.08:1 is achieved. The autoclave is stirred at this temperature for 20 h, subsequently cooled and the residual pressure is released. The reaction mixture is investigated by gas chromatography. 17% of nonanal is determined with an n:iso ratio of 73:27. 40% of octane is detected as hydrogenated starting substance.

The unsaturated starting compounds, the products obtained and the further corresponding parameters are presented in the examples of Table 3 below.

The column n/iso shows the proportions of product having a terminal aldehyde group (n) and non-terminal aldehyde group (iso).

The general reaction course is shown in the equation below. The substituents R$_1$, R$_2$ and R$_3$ correspond to the groups or parts of the compounds that can be inferred in Examples 28 to 38 from the columns "Substrate" and "Product".

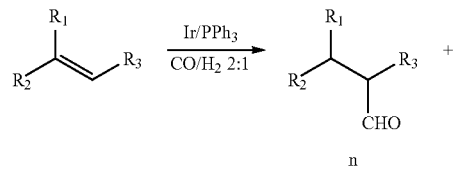

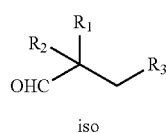

The following general reaction control ([a]) was used for the entries 1-11 of Table 3: 10.2 mmol of substrate, Ir(cod)acac 0.2 mol % (8.1 mg), 0.44 mol % of PPh$_3$ (11.8 mg) and 6 ml of NMP (N-methylpyrrolidone) are transferred to a 25 ml autoclave under protective gas (e.g. argon or nitrogen). 0.7 MPa of carbon monoxide (CO) is injected at 20° C. Subsequently, the mixture is heated to 100° C. and 1.3 MPa of synthesis gas (CO:H$_2$=1:1) are additionally injected at this temperature. A final pressure of the reaction of 2.3 MPa at a CO:H$_2$ ratio of 2.08:1 is achieved. The mixture is stirred for the specified reaction time. Subsequently, the autoclave is cooled and the residual pressure is released. 1 ml of isooctane is added as an internal standard of the reaction mixture and this reaction mixture is investigated by gas chromatography.

TABLE 3

Iridium-catalysed hydroformylation with a preformation step of terminal alkenes, cycloalkenes and aromatic olefins

| No.[a] | Substrate | Product | t [h] | Yield[e] [mass %] | n/iso | H[g] [mass %] |
|---|---|---|---|---|---|---|
| 1 | styrene | 2-phenylpropanal | 24 | 62 | 26/74 | 6 |
| 2 | allylbenzene | 4-phenylbutanal | 16 | 85 | 68/32 | 8 |
| 3 | 4-methoxyallylbenzene | 4-(4-methoxyphenyl)butanal | 16 | 90[f] | 68/32[f] | 9[e] |
| 4[b] | cyclooctene | cyclooctanecarbaldehyde | 48 | 90 | — | 5 |
| 5 | vinylcyclohexane | 3-cyclohexylpropanal | 16 | 90 | 84/16 | 7 |

TABLE 3-continued

Iridium-catalysed hydroformylation with a preformation step of terminal alkenes, cycloalkenes and aromatic olefins

| No.[a] | Substrate | Product | t [h] | Yield[e] [mass %] | n/iso | H[g] [mass %] |
|---|---|---|---|---|---|---|
| 6 | (4-vinylcyclohexene) | (corresponding aldehyde) CHO | 16 | 82 | 79/21 | 9 |
| 7 | (pentene) | CHO | 20 | 71 | 75/25 | 5 |
| 8 | (3,3-dimethylbutene) | CHO | 20[d] 20[a] | 69 62 | 96/4 97/3 | 9 7 |
| 9 | 1-Dodecene[c] | 1-Tridecanal | 20 | 87 | 75/25 | 7 |
| 10 | 1-Octene | 1-Nonanal | 16 | 89 | 76/24 | 6 |
| 11 | (internal octene) | CHO | 20[d] | 14 | 4/96 | 2 |

[a]10.2 mmol of substrate, Ir(cod)acac 0.2 mol % (8.1 mg), 0.44 mol % of PPh₃ (11.8 mg), 6 ml of NMP, 0.7 MPa of CO at room temperature and 1.3 MPa of synthesis gas as 100° C.
[b]as [a] but 0.4% Ir(cod)acac, 0.88 mol % of PPh₃, 130° C.
[c]as [a] but substrate contains 2% dodecane, 3% ethyloctene, 2% methylnonene.
[d]as [a], but in THF.
[e]Yields were determined by gas chromatography.
[f]Yield and n/iso selectivity are determined by NMR.
[g]hydrogenated starting substance.

Example 27

Table 3, Entry 1

10.2 mmol of styrene (1.06 g), Ir(cod)acac 0.2 mol % (8.1 mg), 0.44 mol % of PPh₃ (11.8 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas (CO:H₂=1:1) are additionally injected at this temperature. A final pressure of the reaction of 2.3 MPa is achieved and the mixture is stirred for 24 h. After cooling and releasing the residual pressure of the autoclave, the reaction mixture is investigated by gas chromatography. 62% of the corresponding aldehyde with an n:iso ratio of 26:74 is formed.

Example 28

Table 3, Entry 2

10.2 mmol of allylbenzene (1.2 g), Ir(cod)acac 0.2 mol % (8.1 mg), 0.44 mol % of PPh₃ (11.8 mg) and 6 ml of NMP are transferred to a 25 ml autoclave under protective gas (e.g. argon or nitrogen). 7 bar of carbon monoxide are injected at 20° C., the autoclave is subsequently heated to 100° C. and 13 bar of synthesis gas (CO:H₂=1:1) are additionally injected at this temperature. A final pressure of the reaction of 2.3 MPa is achieved and the mixture is stirred for 16 h. After cooling and releasing the residual pressure of the autoclave, the reaction mixture is investigated by gas chromatography. 85% of the corresponding aldehyde with an n:iso ratio of 68:32 is formed.

Example 29

Table 3, Entry 3

10.2 mmol of 1-allyl-4-methoxybenzene (1.5 g), Ir(cod)acac 0.2 mol % (8.1 mg), 0.44 mol % of PPh₃ (11.8 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas (CO:H₂=1:1) are additionally injected at this temperature. A final pressure of the reaction of 2.3 MPa is achieved and the mixture is stirred for 16 h. After cooling and releasing the residual pressure of the autoclave, the reaction mixture is investigated by NMR spectroscopy. 90% of the corresponding aldehyde with an n:iso ratio of 68:32 is formed.

Example 30

Table 3, Entry 4

10.2 mmol of cyclooctene (1.1 g), Ir(cod)acac 0.4 mol % (16.2 mg), 0.88 mol % of PPh₃ (23.6 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas (CO:H₂=1:1) are additionally injected at this temperature. A final pressure of the reaction of 2.3 MPa is achieved and the mixture is stirred for 48 h. After cooling and releasing the residual pressure of the autoclave, the reaction mixture is investigated by gas chromatography. 90% of the corresponding aldehyde is formed.

Example 31

Table 3, Entry 5

10.2 mmol of vinylcyclohexane (1.1 g), Ir(cod)acac 0.2 mol % (8.1 mg), 0.44 mol % of $PPh_3$ (11.8 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas ($CO:H_2$=1:1) are additionally injected at this temperature. A final pressure of the reaction of 2.3 MPa is achieved and the mixture is stirred for 16 h. After cooling and releasing the residual pressure of the autoclave, the reaction mixture is investigated by gas chromatography. 90% of the corresponding aldehyde with an n:iso ratio of 84:16 is formed.

Example 32

Table 3, Entry 6

10.2 mmol of 1-vinylcyclohex-3-ene (1.1 g), Ir(cod)acac 0.2 mol % (8.1 mg), 0.44 mol % of $PPh_3$ (11.8 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas ($CO:H_2$=1:1) are additionally injected at this temperature. A final pressure of the reaction of 2.3 MPa is achieved and the mixture is stirred for 16 h. After cooling and releasing the residual pressure of the autoclave, the reaction mixture is investigated by gas chromatography. 82% of the corresponding aldehyde with an n:iso ratio of 79:21 is formed.

Example 33

Table 3, Entry 7

10.2 mmol of 1-pentene (0.7 g), Ir(cod)acac 0.2 mol % (8.1 mg), 0.44 mol % of $PPh_3$ (11.8 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas ($CO:H_2$=1:1) are additionally injected at this temperature. A final pressure of the reaction of 2.3 MPa is achieved and the mixture is stirred for 20 h. After cooling and releasing the residual pressure of the autoclave, the reaction mixture is investigated by gas chromatography. 71% of the corresponding aldehyde with an n:iso ratio of 75:25 is formed.

Example 34

Table 3, Entry 8

10.2 mmol of 3,3-dimethyl-1-butene (0.85 g), Ir(cod)acac 0.2 mol % (8.1 mg), 0.44 mol % of $PPh_3$ (11.8 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas ($CO:H_2$=1:1) are additionally injected at this temperature. A final pressure of the reaction of 2.3 MPa is achieved and the mixture is stirred for 20 h. After cooling and releasing the residual pressure of the autoclave, the reaction mixture is investigated by gas chromatography. 62% of the corresponding aldehyde with an n:iso ratio of 97:3 is formed.

Example 35

Table 3, Entry 9

10.2 mmol of 1-dodecene (1.4 g), Ir(cod)acac 0.2 mol % (8.1 mg), 0.44 mol % of $PPh_3$ (11.8 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas ($CO:H_2$=1:1) are additionally injected at this temperature. A final pressure of the reaction of 2.3 MPa is achieved and the mixture is stirred for 20 h. After cooling and releasing the residual pressure of the autoclave, the reaction mixture is investigated by gas chromatography. 87% of the corresponding aldehyde with an n:iso ratio of 75:25 is formed.

Example 36

Table 3, Entry 10

10.2 mmol of 1-octene (1.1 g), Ir(cod)acac 0.2 mol % (8.1 mg), 0.44 mol % of $PPh_3$ (11.8 mg) and 6 ml of NMP are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas ($CO:H_2$=1:1) are additionally injected at this temperature. A final pressure of the reaction of 2.3 MPa is achieved and the mixture is stirred for 16 h. After cooling and releasing the residual pressure of the autoclave, the reaction mixture is investigated by gas chromatography. 89% of the corresponding aldehyde is formed with an n:iso ratio of 76:24.

Example 37

Table 3, Entry 11

10.2 mmol of 2-octene (1.1 g), Ir(cod)acac 0.2 mol % (8.1 mg), 0.44 mol % of $PPh_3$ (11.8 mg) and 6 ml of THF are transferred to a 25 ml autoclave under protective gas (e.g. argon or nitrogen). 0.7 MPa of carbon monoxide is injected at 20° C., the autoclave is subsequently heated to 100° C. and 1.3 MPa of synthesis gas ($CO:H_2$=1:1) are additionally injected at this temperature. A final pressure of the reaction of 2.3 MPa is achieved and the mixture is stirred for 20 h. After cooling and releasing the residual pressure of the autoclave, the reaction mixture is investigated by gas chromatography. 14% of the corresponding aldehyde is formed with an n:iso ratio of 4:96.

The very good yields and selectivities for the method according to the invention are clearly discernible from the examples. Reaction control using a preformation step in the presence of pure carbon monoxide or the injection of a synthesis gas mixture of carbon monoxide and hydrogen at reaction temperature is to be regarded as essential for good yields.

The invention claimed is:

1. A method for hydroformylating an unsaturated compound with a synthesis gas mixture comprising carbon monoxide and hydrogen, the method comprising:
   (a1) heating the unsaturated compound and a catalyst to a reaction temperature of 60 to 200° C. and
   (a2) adding the synthesis gas
   or
   (b1) contacting the unsaturated compound and the catalyst with pure carbon monoxide at normal temperature in a preformation step, (b2) heating the mixture to a reaction temperature of 60 to 200° C. and (b3) on reaching the reaction temperature, replacing the carbon monoxide with the synthesis gas mixture, where a reaction pressure is in a range from 0.1 to 20.0 MPa, a $CO:H_2$ molar ratio in the synthesis gas mixture is in a range from 1:1 to 50:1 and the unsaturated compound is reacted in the presence of a polar solvent and of the catalyst, wherein the catalyst is an iridium catalyst comprising a ligand comprising phosphorus, wherein an iridium:ligand molar ratio is in a range from 1:1 to 1:100.

2. The method of claim 1, wherein the $CO:H_2$ molar ratio in the synthesis gas mixture is in a range from 1:1 to 10:1.

3. The method of claim 1, wherein the unsaturated compound is at least one selected from the group consisting of a terminal alkene, a cycloalkene, and an aromatic olefin having a carbon number between 2 and 20.

4. The method of claim 1, wherein the polar solvent is water or an inert organic solvent.

5. The method of claim 1, wherein a precursor salt or complex comprising iridium forms a catalytically active iridium(hydrido)(carbonyl) complex with the synthesis gas mixture and the ligand comprising phosphorus.

6. The method of claim 5, wherein the precursor salt or complex comprises an Ir(I) halide, an Ir(II) halide, an Ir(I) carboxylate, an Ir(III) carboxylate, an Ir(III) iridate, or an Ir(IV) iridate, wherein iridium is present in an Ir-carbonyl, Ir-olefin, Ir-hydrido, Ir-arene or Ir-allyl complex in an oxidation state of −I to +V.

7. The method of claim 1, wherein the ligand comprising phosphorus forms a monodentate or multidentate bond to an iridium center of the iridium catalyst, and the ligand is at least one selected from the group consisting of a phosphine, a phosphite, a phosphoramidite, a phosphonite, a phosphinite, a triarylphosphine, a trialkylphosphine, Xanthphos ((9,9-dimethyl-9H-xanthen-4,5-diyl)bis(diphenylphosphine)), BINAP (2,2'-bis(diphenylphosphino)-1,1'-binaphthyl), and NaPhos (2,2'-bis((diphenylphosphino)methyl)-1,1'-binaphthyl).

8. The method of claim 1, wherein the reaction is carried out at a reaction temperature of 80 to 200° C.

9. The method of claim 1, wherein the reaction pressure is from 0.1 to 10.0 MPa.

10. The method of claim 1, wherein the iridium:ligand molar ratio is in a range from 1:1 to 1:50.

11. The method of claim 1, wherein the ligand comprising phosphorus is selected from the group consisting of triphenylphosphine, 2-(diphenylphosphino)-1-phenyl-1H-pyrrole, tricyclohexylphosphine and (11bS)-4-tert-butyl-4,5-dihydro-3H-dinaphtho[2,1-c:1',2'-e]phosphepine.

12. The method of claim 3, wherein 0.02 to 0.4 mol % of iridium is employed based on the olefin.

13. The method of claim 1, wherein the unsaturated compound is at least one selected from the group consisting of a terminal alkene, a cycloalkene, and an aromatic olefin having a carbon number of 4 to 12.

14. The method of claim 1, wherein the reaction is carried out at a reaction temperature of 80 to 180° C.

15. The method of claim 1, wherein the reaction is carried out at a reaction temperature of 100 to 160° C.

16. The method of claim 1, wherein the reaction pressure is from 1.0 to 5.0 MPa.

17. The method of claim 1, wherein the iridium:ligand molar ratio is in a range from 1:1 to 1:8.

18. The method of claim 1, wherein the unsaturated compound is a terminal alkene having a carbon number between 2 and 20.

19. The method of claim 1, wherein the unsaturated compound is a cycloalkene having a carbon number between 2 and 20.

20. The method of claim 1, wherein the unsaturated compound is an aromatic olefin having a carbon number between 2 and 20.

* * * * *